United States Patent
Gao et al.

(10) Patent No.: US 8,728,108 B2
(45) Date of Patent: May 20, 2014

(54) SYSTEMS AND METHODS FOR DYNAMIC PNEUMATIC VALVE DRIVER

(75) Inventors: Shawn X. Gao, Irvine, CA (US); Mark Alan Hopkins, Mission Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 554 days.

(21) Appl. No.: 12/944,039

(22) Filed: Nov. 11, 2010

(65) Prior Publication Data

US 2011/0144675 A1   Jun. 16, 2011

Related U.S. Application Data

(60) Provisional application No. 61/285,243, filed on Dec. 10, 2009.

(51) Int. Cl.
*A61F 9/00* (2006.01)
*F16K 31/36* (2006.01)

(52) U.S. Cl.
USPC .................................... 606/166; 137/487.5

(58) Field of Classification Search
USPC ......... 606/159, 160, 170, 171, 175, 176, 178, 606/179, 180, 167, 166; 137/557, 624.12, 137/624.18; 604/22
See application file for complete search history.

(56) References Cited

U.S. PATENT DOCUMENTS

| | | | |
|---|---|---|---|
| 812,162 A | 2/1906 | Bemis | |
| 2,016,746 A | 10/1935 | Ireland | |
| 2,707,389 A | 5/1955 | Fortier | |
| 3,084,674 A | 4/1963 | Watson | |
| 3,477,665 A | 11/1969 | Legrand | |
| 3,646,727 A | 3/1972 | Wachsmuth | |
| 3,703,139 A | 11/1972 | Furlong | |
| 3,815,604 A | 6/1974 | O'Malley et al. | |
| 3,854,382 A | 12/1974 | Walters et al. | |
| 3,867,934 A | 2/1975 | Ollivier | |
| 4,011,869 A | 3/1977 | Seiler, Jr. | |
| 4,077,567 A | 3/1978 | Ginn et al. | |

(Continued)

FOREIGN PATENT DOCUMENTS

DE   3708989   10/1988
DE   3925405 A1   2/1991

(Continued)

OTHER PUBLICATIONS

International Searching Authority, International Search Report, PCT/US2010/056305, Mar. 2, 2011, 3 pages.

(Continued)

*Primary Examiner* — Tuan V Nguyen

(57) ABSTRACT

In various embodiments, a pneumatic system valve for a surgical console may be controlled by a controller configured to adjust a valve duty cycle (VDC) of the valve to reduce a difference between the valve's differential pressure and a desired differential pressure. In some embodiments, average differential pressures may be detected and relayed from a pressure sensor, coupled to one or more ports of the valve, to the controller. The controller may compare the measured average differential pressure against the desired average differential pressure (e.g., received from the user). The controller may then determine a modified VDC to reduce a difference between the desired average differential pressure and the measured average differential pressure. In some embodiments, the desired average differential pressure may be determined based on input received from a user of the surgical console.

11 Claims, 7 Drawing Sheets

(56) References Cited

U.S. PATENT DOCUMENTS

| | | | |
|---|---|---|---|
| 4,086,804 A | 5/1978 | Ruby | |
| 4,164,167 A | 8/1979 | Imai et al. | |
| 4,168,707 A | 9/1979 | Douvas et al. | |
| 4,253,480 A | 3/1981 | Kessel et al. | |
| 4,323,064 A | 4/1982 | Hoenig et al. | |
| 4,331,130 A | 5/1982 | Lewicky | |
| 4,335,867 A | 6/1982 | Bihlmaier | |
| 4,344,144 A | 8/1982 | Damico et al. | |
| 4,368,734 A | 1/1983 | Banko | |
| 4,373,549 A * | 2/1983 | Nalepa et al. | 137/487.5 |
| 4,476,532 A | 10/1984 | Akiyama et al. | |
| 4,590,935 A | 5/1986 | Ranalli | |
| 4,622,503 A | 11/1986 | Sundblom et al. | |
| 4,650,460 A | 3/1987 | Roizenblatt | |
| 4,650,462 A | 3/1987 | DeSatnick et al. | |
| 4,678,459 A | 7/1987 | Onik et al. | |
| 4,679,583 A | 7/1987 | Lucas et al. | |
| 4,696,298 A | 9/1987 | Higgins et al. | |
| 4,706,687 A | 11/1987 | Rogers et al. | |
| 4,757,814 A | 7/1988 | Wang et al. | |
| 4,770,654 A | 9/1988 | Rogers et al. | |
| 4,790,816 A | 12/1988 | Sundblom et al. | |
| 4,810,242 A | 3/1989 | Sundblom et al. | |
| 4,840,111 A | 6/1989 | Garnjost | |
| 4,933,843 A | 6/1990 | Scheller et al. | |
| 4,985,027 A | 1/1991 | Dressel | |
| 5,019,035 A | 5/1991 | Missirlian et al. | |
| 5,020,315 A | 6/1991 | Leachman, Jr. et al. | |
| 5,020,825 A | 6/1991 | Lizell | |
| 5,024,654 A | 6/1991 | Tyler | |
| 5,047,008 A | 9/1991 | de Juan, Jr. et al. | |
| 5,092,178 A | 3/1992 | Vanderlaan | |
| 5,094,260 A | 3/1992 | Stuart et al. | |
| 5,106,364 A | 4/1992 | Hayafuji et al. | |
| 5,138,564 A | 8/1992 | de Jong et al. | |
| 5,154,207 A | 10/1992 | Bolt | |
| 5,176,628 A | 1/1993 | Charles et al. | |
| 5,217,465 A | 6/1993 | Steppe | |
| 5,239,861 A | 8/1993 | Fujita et al. | |
| 5,314,295 A | 5/1994 | Lukkari et al. | |
| 5,380,280 A | 1/1995 | Peterson | |
| 5,403,276 A | 4/1995 | Schechter et al. | |
| 5,417,246 A | 5/1995 | Perkins et al. | |
| 5,437,241 A | 8/1995 | Rosenberg et al. | |
| 5,445,773 A | 8/1995 | Arai | |
| 5,457,625 A | 10/1995 | Lim et al. | |
| 5,549,139 A | 8/1996 | Perkins et al. | |
| 5,550,685 A | 8/1996 | Drouin | |
| 5,571,248 A | 11/1996 | Seetharaman et al. | |
| 5,580,347 A | 12/1996 | Reimels | |
| 5,587,536 A | 12/1996 | Rasmussen | |
| 5,630,827 A | 5/1997 | Vijfvinkel | |
| 5,674,194 A | 10/1997 | Jung et al. | |
| 5,791,142 A | 8/1998 | Layne et al. | |
| 5,808,396 A | 9/1998 | Boukhny | |
| 5,810,765 A | 9/1998 | Oda | |
| 5,829,335 A | 11/1998 | Ewald et al. | |
| 5,846,257 A | 12/1998 | Hood | |
| 5,857,485 A | 1/1999 | Perkins et al. | |
| 5,959,390 A | 9/1999 | Boukhny | |
| 5,979,494 A | 11/1999 | Perkins et al. | |
| 5,989,262 A | 11/1999 | Josephberg | |
| 5,993,409 A | 11/1999 | Maaskamp | |
| 6,155,233 A | 12/2000 | Wade et al. | |
| 6,162,187 A | 12/2000 | Buzzard et al. | |
| 6,425,883 B1 | 7/2002 | Urich et al. | |
| 6,450,966 B1 | 9/2002 | Hanna | |
| 6,485,436 B1 | 11/2002 | Truckai et al. | |
| 6,514,268 B2 | 2/2003 | Finlay et al. | |
| 6,575,264 B2 | 6/2003 | Spadafora | |
| 6,575,990 B1 | 6/2003 | Wang et al. | |
| 6,678,584 B2 | 1/2004 | Junk et al. | |
| 6,730,106 B2 | 5/2004 | Kanda et al. | |
| 6,773,445 B2 | 8/2004 | Finlay et al. | |
| 6,779,541 B2 | 8/2004 | Inayama et al. | |
| 6,848,323 B2 | 2/2005 | Krouth et al. | |
| 6,851,453 B2 | 2/2005 | Lipscomb et al. | |
| 6,892,745 B2 | 5/2005 | Benson | |
| 6,954,683 B2 | 10/2005 | Junk et al. | |
| 6,999,853 B2 | 2/2006 | Junk et al. | |
| 7,244,240 B2 | 7/2007 | Nazarifar et al. | |
| 7,263,877 B2 | 9/2007 | Schaefer et al. | |
| 7,283,321 B1 | 10/2007 | Sun et al. | |
| 7,335,217 B2 | 2/2008 | Wang et al. | |
| 7,337,041 B2 | 2/2008 | Junk et al. | |
| 7,352,287 B2 | 4/2008 | Rupert | |
| 7,470,277 B2 | 12/2008 | Finlay et al. | |
| 7,600,405 B2 | 10/2009 | Maurer, Jr. et al. | |
| 7,628,054 B2 | 12/2009 | Hajishah et al. | |
| 7,640,119 B2 | 12/2009 | Khashayar | |
| 7,708,734 B2 | 5/2010 | Khashayar | |
| 7,775,052 B2 | 8/2010 | Cornwell et al. | |
| 8,038,692 B2 | 10/2011 | Valencia et al. | |
| 8,157,145 B2 | 4/2012 | Shelton, IV et al. | |
| 8,187,293 B2 | 5/2012 | Kirchhevel | |
| 8,202,277 B2 | 6/2012 | Ryan | |
| 8,215,108 B2 | 7/2012 | Hahn et al. | |
| 8,230,877 B2 | 7/2012 | Roberge et al. | |
| 8,308,737 B2 | 11/2012 | Ryan | |
| 2002/0117214 A1 | 8/2002 | Tucker et al. | |
| 2003/0042182 A1 | 3/2003 | Moscaritolo | |
| 2003/0195538 A1 | 10/2003 | Wang et al. | |
| 2003/0208305 A1 | 11/2003 | Junk et al. | |
| 2004/0154466 A1 | 8/2004 | Gethmann et al. | |
| 2004/0186484 A1 | 9/2004 | Ryan | |
| 2005/0033309 A1 | 2/2005 | Ryan | |
| 2005/0245909 A1 | 11/2005 | McCary et al. | |
| 2006/0129062 A1 | 6/2006 | Nicoson et al. | |
| 2006/0271082 A1 | 11/2006 | Kirchhevel et al. | |
| 2007/0093793 A1 | 4/2007 | Maurer, Jr. et al. | |
| 2007/0185512 A1 | 8/2007 | Kirchhevel | |
| 2007/0219647 A1 | 9/2007 | Heertjes et al. | |
| 2007/0270735 A1 | 11/2007 | Williams et al. | |
| 2007/0270746 A1 | 11/2007 | King | |
| 2007/0282262 A1 | 12/2007 | Williams et al. | |
| 2008/0082077 A1 | 4/2008 | Williams | |
| 2008/0103433 A1 | 5/2008 | Nazarifar et al. | |
| 2008/0108980 A1 | 5/2008 | Turner et al. | |
| 2008/0110236 A1 | 5/2008 | Hajishah et al. | |
| 2008/0142093 A1 | 6/2008 | Turner et al. | |
| 2008/0146988 A1 | 6/2008 | Olivera et al. | |
| 2008/0149197 A1 | 6/2008 | Turner et al. | |
| 2008/0168985 A1 | 7/2008 | Turner et al. | |
| 2008/0172077 A1 | 7/2008 | Valencia et al. | |
| 2008/0300580 A1 | 12/2008 | Shelton, IV et al. | |
| 2009/0082715 A1 | 3/2009 | Charles et al. | |
| 2009/0124962 A1 | 5/2009 | Hopkins et al. | |
| 2009/0203480 A1 | 8/2009 | Petzold et al. | |
| 2009/0259242 A1 | 10/2009 | Gerg et al. | |
| 2009/0287233 A1 | 11/2009 | Huculak | |
| 2009/0305214 A1 | 12/2009 | Pybus et al. | |
| 2010/0145374 A1 | 6/2010 | Perkins et al. | |
| 2010/0305596 A1 | 12/2010 | Peterson et al. | |
| 2010/0312169 A1 | 12/2010 | Auld et al. | |
| 2011/0005387 A1 | 1/2011 | Ehre et al. | |
| 2011/0054508 A1 | 3/2011 | Zhou et al. | |
| 2011/0295293 A1 | 12/2011 | Agahi | |
| 2011/0299943 A1 | 12/2011 | Woolever | |
| 2012/0010602 A1 | 1/2012 | Ryan | |
| 2012/0055329 A1 | 3/2012 | Heer | |
| 2012/0157906 A1 | 6/2012 | Underwood | |
| 2012/0157907 A1 | 6/2012 | Underwood | |
| 2012/0157908 A1 | 6/2012 | Underwood | |
| 2012/0157909 A1 | 6/2012 | Underwood | |
| 2012/0158006 A1 | 6/2012 | MdDonell | |
| 2012/0158029 A1 | 6/2012 | Underwood | |
| 2012/0158030 A1 | 6/2012 | Underwood | |
| 2012/0221033 A1 | 8/2012 | Auld | |

FOREIGN PATENT DOCUMENTS

| | | |
|---|---|---|
| DE | 4232586 A1 | 3/1994 |
| DE | 19821420 C1 | 10/1999 |
| DE | 10247869 A1 | 5/2004 |

(56) References Cited

FOREIGN PATENT DOCUMENTS

| | | |
|---|---|---|
| DE | 202005009670 U1 | 9/2005 |
| DE | 10247869 B4 | 2/2007 |
| DE | 102006030034 | 1/2008 |
| EP | 0469641 B1 | 6/1989 |
| EP | 0626628 A1 | 11/1994 |
| EP | 0673475 B1 | 6/1996 |
| EP | 0626628 B1 | 12/1997 |
| EP | 0874163 A2 | 10/1998 |
| EP | 0884667 A1 | 12/1998 |
| EP | 0874163 A3 | 3/1999 |
| EP | 1074271 A2 | 2/2001 |
| EP | 1074271 A3 | 2/2002 |
| EP | 1172586 B1 | 3/2004 |
| EP | 1074271 B1 | 10/2004 |
| EP | 1660244 B1 | 12/2006 |
| EP | 2032878 B1 | 12/2009 |
| GB | 792397 A | 3/1958 |
| GB | 1189493 A | 6/1970 |
| GB | 1213723 A | 11/1970 |
| GB | 1 323 788 A | 7/1973 |
| GB | 1417299 A | 12/1975 |
| GB | 2016746 A | 9/1979 |
| GB | 2 140 871 A | 12/1984 |
| GB | 2203195 A | 10/1988 |
| GB | 2389423 A | 12/2003 |
| JP | 07259801 A | 10/1995 |
| JP | 09225698 A | 9/1997 |
| JP | 9311091 A | 12/1997 |
| JP | 2010057642 A | 3/2010 |
| WO | 92/02866 A1 | 2/1992 |
| WO | 93/18445 A1 | 9/1993 |
| WO | WO 9531141 A1 | 11/1995 |
| WO | 98/25556 A1 | 6/1998 |
| WO | WO 00/78371 A1 | 12/2000 |
| WO | WO 0130281 A1 | 5/2001 |
| WO | WO 0164120 A1 | 9/2001 |
| WO | WO 2008/000599 A1 | 1/2008 |
| WO | 2008/029066 A1 | 3/2008 |
| WO | WO 2008054944 A1 | 5/2008 |
| WO | WO 2008079526 A2 | 7/2008 |
| WO | WO 2008079526 A3 | 8/2008 |
| WO | WO 2008105950 A2 | 9/2008 |
| WO | WO 2008140537 A1 | 11/2008 |
| WO | WO 2008147429 A2 | 12/2008 |
| WO | WO 2008147429 A3 | 3/2009 |
| WO | WO 2008105950 A3 | 9/2009 |
| WO | WO 2010/066302 A1 | 6/2010 |
| WO | WO 2011/025658 A1 | 3/2011 |
| WO | 2011071613 A1 | 6/2011 |
| WO | WO 2011/071655 A1 | 6/2011 |
| WO | 2011138102 A1 | 11/2011 |
| WO | WO 2011/149621 A1 | 12/2011 |

OTHER PUBLICATIONS

International Searching Authority, Written Opinion of the International Searching Authority, PCT/US2010/056305, Mar. 2, 2011, 7 pages.
International Searching Authority, International Search Report, PCT/US2010/045136, Nov. 18, 2010, 4 pages.
International Searching Authority, Written Opinion of the International Searching Authority, PCT/US2010/045136, Nov. 18, 2010, 6 pages.
Nguyen, Tuan Van, Non-Final Office Action, U.S. Appl. No. 12/788,609, Jan. 18, 2012, 32 pages.
International Searching Authority, International Search Report, PCT/US2011/034720, Jul. 28, 2011, 2 pages.
International Searching Authority, Written Opinion of the International Searching Authority, PCT/US2011/034720, Jul. 20, 2011, 8 pages.
Nguyen, Tuan Van, Non-Final Office Action, U.S. Appl. No. 12/788,609, Jul. 12, 2012, 24 pages.
Kabei, Shimemura, et al., A portable pneumatic driving unit for a left ventricular assist device, Int. J. Artif. Organs, 1988, 186-90, 11(3).
Nachlas, Marvin, et al., A simple portable pneumatic pump for external cardiac massage, The American Journal of Cardiology, 1962, 107-109, 10(1).
Waldeck, J.L., The development of a portable pressure source for the static and dynamic calibration of pressure transducers, The Journal of Wind Engineering and Industrial Aerodynamics, 1987, 213-230, 26(2).
Ellis, George, et al., Microcomputer-Controlled Precision Pressure Generator, IEEE Transactions on Instrumentation and Measurement, 1977, 214-217, 26(3).
Whalen, R.L., et al., An electromagnetic pneumatic blood pump driver, American Society of Artificial Internal Organs, 1988, 721-725, 34(3).
Turkentine, R.B., et al., Pressure-operated shutter for thin-film monitor, Journal of Physics E: Scientific Instruments, 1979, 12(1).
Rogers, Richard C., An inexpensive picoliter-vol. pressure ejection system, Brain Research Bulletin, 1985, 669-671, 15(6).
Johnson, Kenneth S., et al., A submersible flow analysis System, Analytical Chimica Acta, 1986, 245-257, 179.
Tabassum, Alim Abid, Solar refrigeration: evaluation of technical options and design of a solar-generator-adsorber for a novel adsorption refrigerator, Tabassum thesis abstract, Cranfield University, 1989.
Buchanan, P.R., et al., Recovery of ventilation distributions by gas wash-out of a mechanical pump, Clinical Physics and Physiological Measurement, 1986, 7(3).
Agahi, Daryush, "Feedback of On/Off Pneumatic Actuators," U.S. Appl. No. 12/788,609, filed May 27, 2010, 24 pgs.
Zhou, Jason, et al., "Pneumatic Pressure Output Control by Drive Valve Duty Cycle Calibration," U.S. Appl. No. 12/854,281, filed Aug. 11, 2010, 38 pgs.
International Searching Authority, International Search Report, PCT/US2012/049695, Oct. 24, 2012, 2 pages.
International Searching Authority, Written Opinion of the International Searching Authority, PCT/2012/049695, Oct. 24, 2012, 4 pages.

* cited by examiner

| Port Duty Cycle | Average Differential Pressure |
|---|---|
| 70% | 8.0 psi |
| 65% | 5.8 psi |
| 60% | 3.5 psi |
| 55% | 1.3 psi |
| 50% | -1.0 psi |
| 45% | -3.3 psi |
| 40% | -5.5 psi |
| 35% | -7.8 psi |
| 30% | -10.0 psi |

*FIG. 5*

SYSTEMS AND METHODS FOR DYNAMIC PNEUMATIC VALVE DRIVER

PRIORITY

This application claims the benefit of priority of U.S. Provisional Patent Application Ser. No. 61/285,243 titled "Systems and Methods for Dynamic Pneumatic Valve Driver", filed on Dec. 10, 2009, whose inventors are Shawn X. Gao and Mark A. Hopkins, which is hereby incorporated by reference in its entirety as though fully and completely set forth herein.

FIELD OF THE INVENTION

The present invention generally pertains to a pneumatic surgical system. More particularly, but not by way of limitation, the present invention pertains to surgical system pneumatic generation.

DESCRIPTION OF THE RELATED ART

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It may make up approximately ⅔ of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue may obscure light as it passes through the eye to the retina, resulting in blurred vision. The vitreous may also be removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

The retinal surgeon may perform a vitrectomy with a microscope and special lenses designed to provide a clear image of the back of the eye. Several tiny incisions just a few millimeters in length may be made on the sclera. The retinal surgeon may insert microsurgical instruments through the incisions such as a fiber optic light source to illuminate inside the eye, an infusion line to maintain the eye's shape during surgery, and instruments to cut and remove the vitreous.

In a vitrectomy, the surgeon may create three tiny incisions in the eye for three separate instruments. These incisions may be placed in the pars plana of the eye, which is located just behind the iris but in front of the retina. The instruments which pass through these incisions may include a light pipe, an infusion port, and the vitrectomy cutting device. The light pipe is the equivalent of a microscopic high-intensity flashlight for use within the eye. The infusion port may be used to replace fluid in the eye and maintain proper pressure within the eye. The vitrector, or cutting device, may work like a tiny guillotine, with an oscillating microscopic cutter to remove the vitreous gel in a controlled fashion. This may prevent significant traction on the retina during the removal of the vitreous humor.

The surgical machine used to perform a vitrectomy and other surgeries on the posterior of the eye is very complex. Typically, such an ophthalmic surgical machine includes a main console to which the numerous different tools are attached. The main console may provide power to and control the operation of the attached tools.

The attached tools typically include probes, scissors, forceps, illuminators, vitrectors, and infusion lines. Each of these tools is typically attached to the main surgical console. A computer in the main surgical console may monitor and control the operation of these tools. These tools may also get their power from the main surgical console. Some of these tools may be electrically powered while others may be pneumatically powered.

In order to provide pneumatic power to the various tools, the main surgical console may include a pneumatic or air distribution module. This pneumatic module may condition and supply compressed air or gas to power the tools. The pneumatic module may be connected to a cylinder that contains compressed gas. The pneumatic module may provide the proper gas pressure to operate the attached tools properly.

SUMMARY OF THE INVENTION

In various embodiments, a pneumatic system valve for a surgical console may be controlled by a controller configured to adjust a valve duty cycle (VDC) (the VDC being used to energize the valve) to reduce a difference between a differential pressure (e.g., an average differential pressure) at the valve's output and a desired differential pressure (e.g., a desired average differential pressure). In some embodiments, average differential pressures may be detected and relayed from a pressure sensor, coupled to one or more ports of the valve, to the controller (e.g., implementing a PID controller (Proportional-Integral-Derivative controller) algorithm). The controller may compare the measured average differential pressure against the desired average differential pressure (e.g., received from the user or determined based on information received from the user). The controller may then determine a modified VDC to reduce a difference between the desired average differential pressure and the measured average differential pressure. In some embodiments, multiple iterations may be performed to reduce the difference between the measured average differential pressure and the desired average differential pressure.

BRIEF DESCRIPTION OF THE DRAWINGS

For a more complete understanding of the present invention, reference is made to the following description taken in conjunction with the accompanying drawings in which:

FIG. 5 illustrates an embodiment of a look-up table for correlating port duty cycle with average differential pressure, according to an embodiment.

It is to be understood that both the foregoing general description and the following detailed description are exemplary and explanatory only and are intended to provide a further explanation of the present invention as claimed.

DETAILED DESCRIPTION OF THE EMBODIMENTS

U.S. Patent Application Publication entitled "Pneumatic System for a Vitrector," Publication No. 20080149197, Ser. No. 11/614,678, by Denis Turner, Robert Palino, Argelio Olivera, and Mark Hopkins filed Dec. 21, 2006 is hereby incorporated by reference in its entirety as though fully and completely set forth herein.

Figure 1:
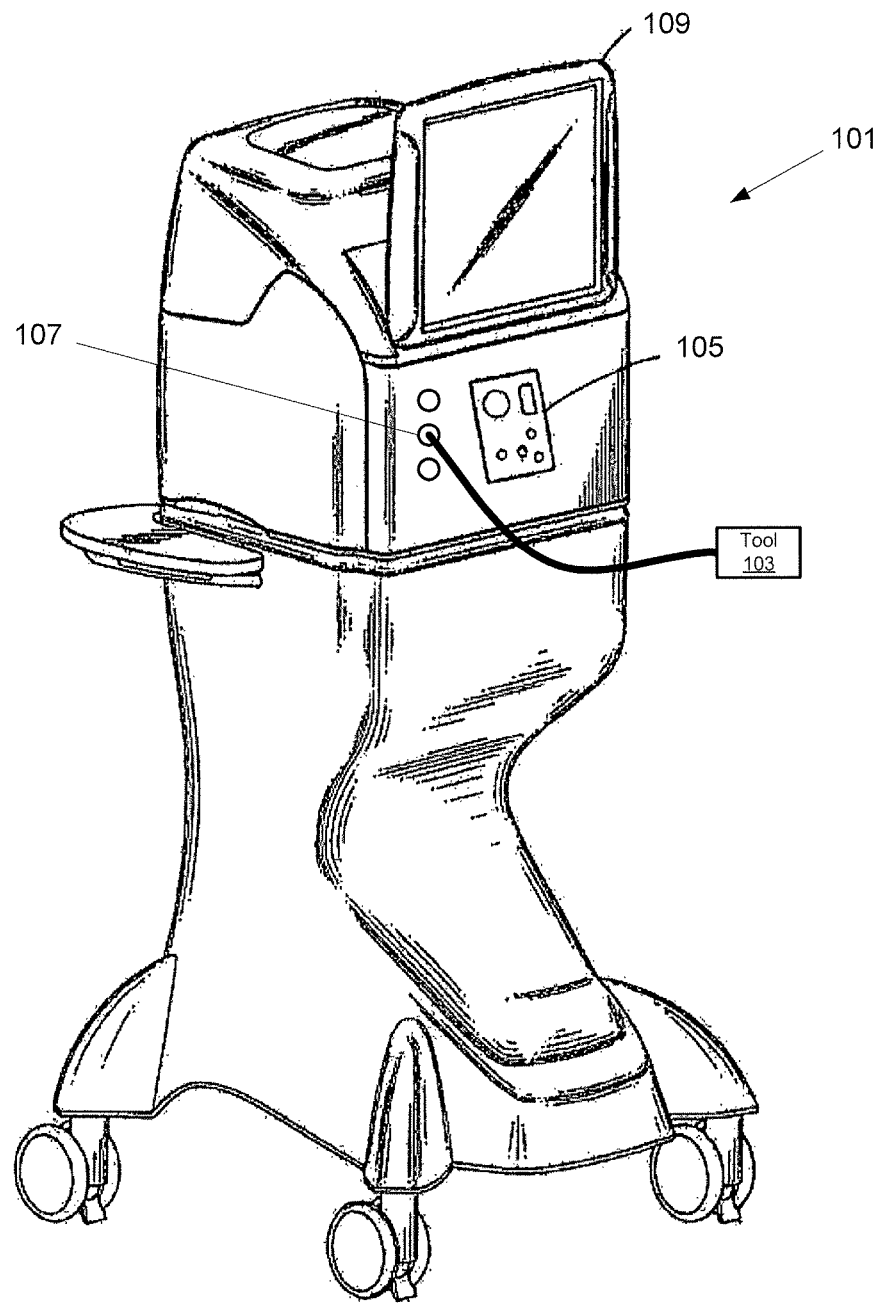
FIG. 1 is surgical console, according to an embodiment.

FIG. 1 illustrates an embodiment of a surgical console 101 for a pneumatically powered ophthalmic surgical machine. The surgical console 101 may be configured to drive one or more pneumatic tools 103. The tools 103 may include, for example, scissors, vitrectors, forceps, and injection or extraction modules. Other tools 103 may also be used. In operation, the pneumatically powered ophthalmic surgery machine of FIG. 1 may operate to assist a surgeon in performing various ophthalmic surgical procedures, such as a vitrectomy. A compressed gas, such as nitrogen, may provide the power through the surgical console 101 to power tools 103. The surgical console 101 may include a display 109 for displaying information to a user (the display may also incorporate a touchscreen for receiving user input). The surgical console 101 may also include a fluidics module 105 (e.g., to support irrigation/aspiration functions) and one or more port connectors 107 for coupling to tools 103 (e.g., coupling through pneumatic lines attached to the tools 103).

FIG. 2 is a schematic of a pneumatic system for a pneumatically powered vitrectomy machine, according to an embodiment. As seen in FIG. 2, the pneumatic system may include one or more pneumatic valves 217 coupling a pressure source 209 (e.g., a regulated pressure source such as an air cylinder or a wall outlet air supply) to output port A 213 and output port B 215 (the output port A 213 and output port B 215 may be coupled to the tool 103 through one or more port connectors 107). In some embodiments, the pneumatic valve 217 may be controlled by controller 205. In some embodiments, the pressure of the pressure source 209 may also be regulated by controller 205 or a separate controller (e.g., internal to the surgical console 101). The controller 205 may regulate pressure (e.g., to balance between lower pressures for reducing air consumption and higher pressures for faster cut rates and/or to increase a dynamic range of available cut rates). In some embodiments, the components of the pneumatic system may be incorporated in a manifold (e.g., machined out of a metal, such as aluminum). The manifold may be air tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 101.

In some embodiments, pneumatic valve 217 may be a four-way valve. Other valve configurations are also contemplated. The valve 217 may include a solenoid that operates to move the valve 217 to one of the two positions (e.g., see FIGS. 2a-b) as directed by control signals from controller 205. In a first position, pneumatic valve 217 may allow pressurized gas to pass through pneumatic valve 217 to output port B 215 to provide pneumatic power to the probe cutter 225 while venting pressurized gas from output port A 213 through muffler 227. In a second position, the valve 217 may provide pressurized gas to output port A 213 and vent pressurized gas from output port B 215. In this position, pressurized gas may pass through output port A 213 to provide pneumatic power to a tool 103 (e.g., probe cutter 225). Thus, when the pneumatic valve 217 is in the first position, the first chamber 229 of the dual chambers 223 may be charged while the second chamber 231 may be discharged. When the pneumatic valve 217 is in the second position the second chamber 231 may be charged while the first chamber 229 may be discharged.

Figure 3:
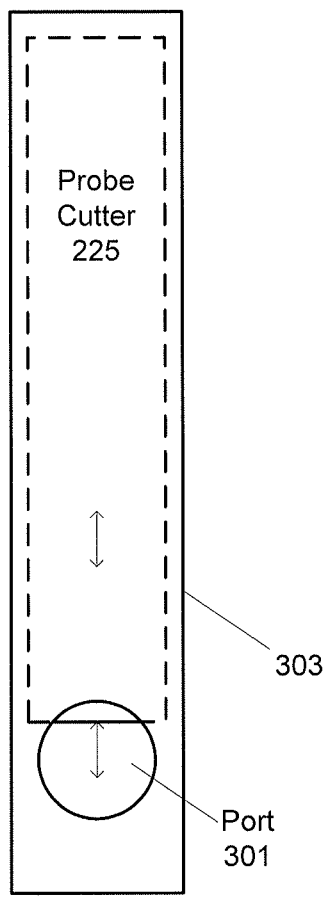
FIG. 3 illustrates a vitrectomy cutter, according to an embodiment.

As seen in FIG. 3, the probe cutter 225 may act as a cutting device. The probe cutter 225 may reciprocate inside an outer tube 303 with a cutter port 301 (e.g., the probe cutter 225 may be moved by a diaphragm 221 that in turn oscillates as pressurized gas is alternately directed to output ports A and B (and into respective chambers of the dual chamber 223)). In some embodiments, probe cutter 225 may be attached to output ports A and B through tube 219 (separate tubes for each port may also be used). As the probe cutter 225 moves back and forth, the probe cutter 225 may alternately open and close cutter port 301 with a sharpened tip of the probe cutter 225. Each cycle of the probe cutter 225 through outer tube 303 may cut through material such as vitreous in the cutter port 301 as the probe cutter 225 is closing. A port duty cycle (PDC) may indicate the amount of time the cutter port 301 is open and closed. For example, a PDC of 49% may indicate the cutter port 301 is open 49% of the cycle time (and closed 51% of the cycle time—the cycle time being, for example, the amount of time between each successive opening of the cutter port 301).

In some embodiments, the valve duty cycle (VDC) may include the amount of time the pneumatic valve 217 is in the first and second positions. In some embodiments, a cut rate of the probe cutter 225 may be controlled by the controller 205 through valve 217. For example, to provide a 2500 cuts per minute probe rate, controller 205 may direct pneumatic valve 217 to provide pressurized air alternately to port A (second channel) and port B (first channel) at a rate of approximately 24 ms per cycle. To obtain a cut rate of 2500 cuts per minute, the two pneumatic channels may cycle open/closed every 24 ms (2500 cuts/min or 1 min/2500 cuts*60 seconds/1 min=0.024 seconds/cut=24 ms/cut), which may open for 12 ms to each channel. In some embodiments, a transition time to actually open and close the channels may use part of the cycle time. For example, pneumatic second channel (i.e., via port A 213 of pneumatic valve 217) may take 4 ms to open (while pneumatic first channel is closing) and 2 ms to close (while pneumatic first channel is opening) for a total transition time per 24 ms cycle of 6 ms. Other transition times are also contemplated. Because of the transition time, the valve may actually be open only 8 ms (12 ms−4 ms) to second channel while closed to first channel and may be closed for 10 ms (12 ms−2 ms) to second channel while open to first channel. This valve timing difference of 8 ms vs. 10 ms in providing pressurized air to second channel and first channel may result in an unbalanced pressure differential in the two channels. In some embodiments, it may be desirable for the open time durations of the two channels to be approximately the same (e.g., in the case of 2500 cuts/minute, actually open for approximately (24 ms−6 ms)/2=9 ms).

If the open/close transition timings were constant for all pneumatic valves 217 then the controller 205 could be preprogrammed with a fixed valve duty cycle to achieve approximately equal actual open time durations for both channels based on a standard pneumatic valve 217. For example, the nominal open time may be set to 13 ms for second channel and 11 ms for first channel. Thus, for this example, excluding transition time, the actual open time of the second channel may be 13 ms−4 ms=9 ms and the actual open time of the first channel may be 11 ms−2 ms=9 ms (similar to second channel). However, because the transition time may vary between various pneumatic valves 217 (e.g., due to manufacturing variances, flow restrictions, temperature, aging, etc. of pneumatic valve 217), a fixed valve duty cycle may not successfully counter the imbalance. For example, a different valve may take 3 ms (instead of 4 ms) to open the second channel (while the pneumatic first channel is closing) and 2 ms to close the second channel (while the pneumatic first channel is opening). If the same valve duty cycle (e.g., 13 ms nominal open time for the second channel and 11 ms nominal open time for the first channel) was applied to this second valve example, the actual open time for the pneumatic second channel of the second valve would be 13 ms−3 ms=10 ms and the actual open time for the first channel would be 11 ms−2 ms=9 ms. Therefore, the valve duty cycle that worked for the previous valve example results in the pneumatic second channel remaining actually open 1 ms or 11% longer than the pneumatic first channel for the second example valve. The difference may result in an uneven power balance between the two pneumatic channels which may result in less desirable performance. Similarly, a fixed valve duty cycle may not successfully counter the imbalance caused by the flow restriction/resistance variations in the two channels from console to console.

In some embodiments, the effects of the valve variation may be dynamically compensated by monitoring the pressure waveform (e.g., the average differential pressures 207 detected over the run time of the valve by pressure sensor 211 (FIG. 2a) or calculated by the controller using pressure information from pressure sensors 212a,b (FIG. 2b)) at the output of the valve 217. Pressure information may include, for example, detected pressure waveforms at the pressure sensors 212a,b or average pressure readings from the pressure sensors 212a,b (other pressure information is also possible). The pressure sensors 211, 212a,b may include a pressure transducer capable of reading pressure of a compressed gas and sending an electrical signal containing information about the pressure of the compressed gas to the controller 205. The pressure waveform (which may be indicative of the actual VDC) may be monitored (e.g., periodically or continuously monitored) during the run time. The average differential pressures 207 may be used by the controller 205 to compensate for valve variations by modifying the VDC of the valve to reduce a difference between the actual differential pressures and a desired differential pressure. Thus, in some embodiments, a close-loop approach may include monitoring an average of a differential pressure at the output of the pneumatic valve 217 (differential pressure between port A 213 and port B 215) and using the average differential 207 to determine valve specific information for use in controlling the VDC. In some embodiments, the average differential pressure 207 over a cycle period (1/cutrate) ay be directly related to the VDC and may be used by the controller 205 to dynamically adjust the VDC of the control signal sent to the pneumatic valve 217. In some embodiments, an actual differential pressure may not be calculated, but instead the controller may compare pressure information from the pressure sensors 212a,b to dynamically adjust the VDC. For example, a comparison of the pressure waveforms (or average pressures) from port A and port B may indicate a difference that can be countered by adjusting the VDC. Other VDC adjustments are also possible.

Figure 2A:
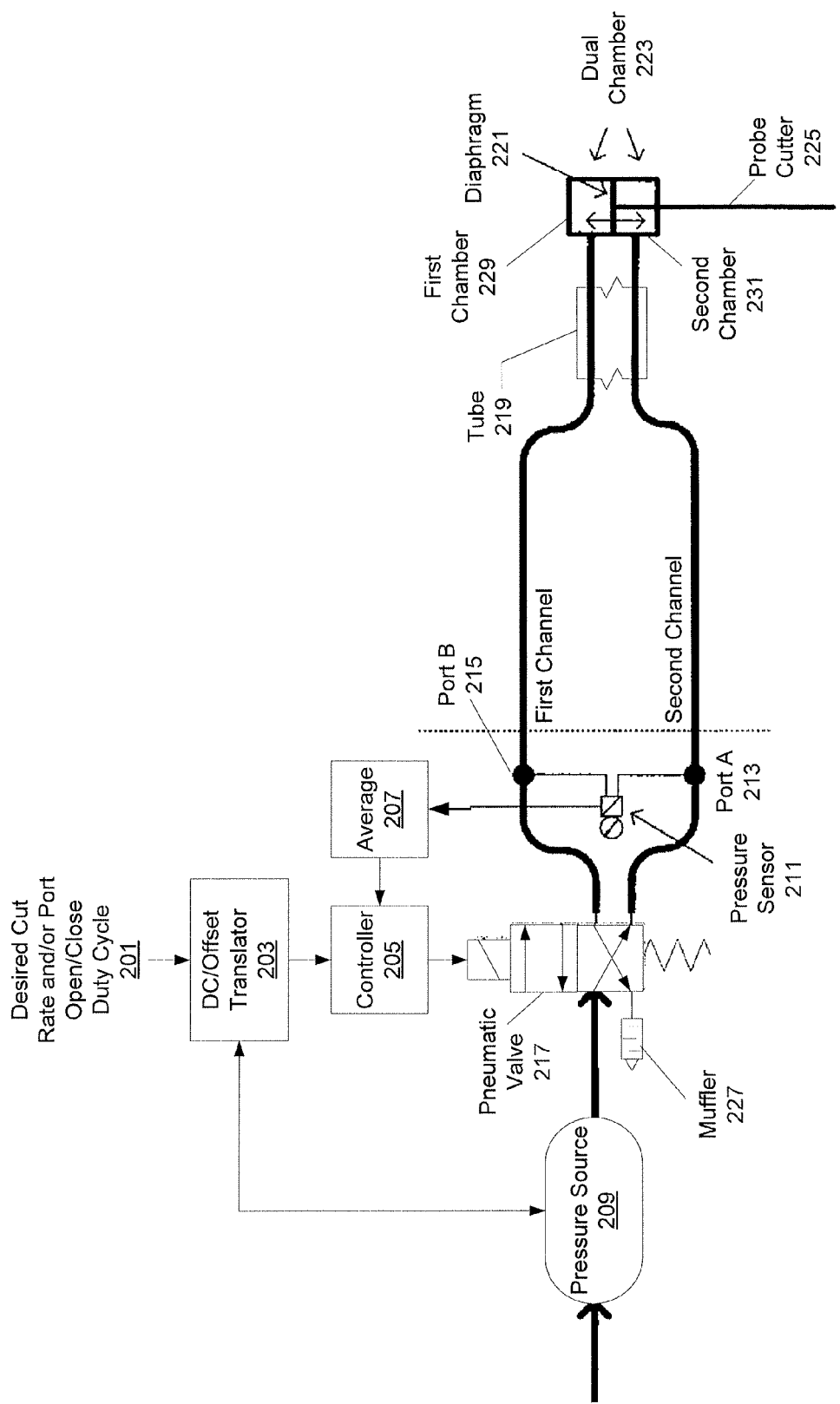
FIG. 2a is diagram of a pneumatic system with a differential pressure sensor, according to an embodiment.
Figure 2B:
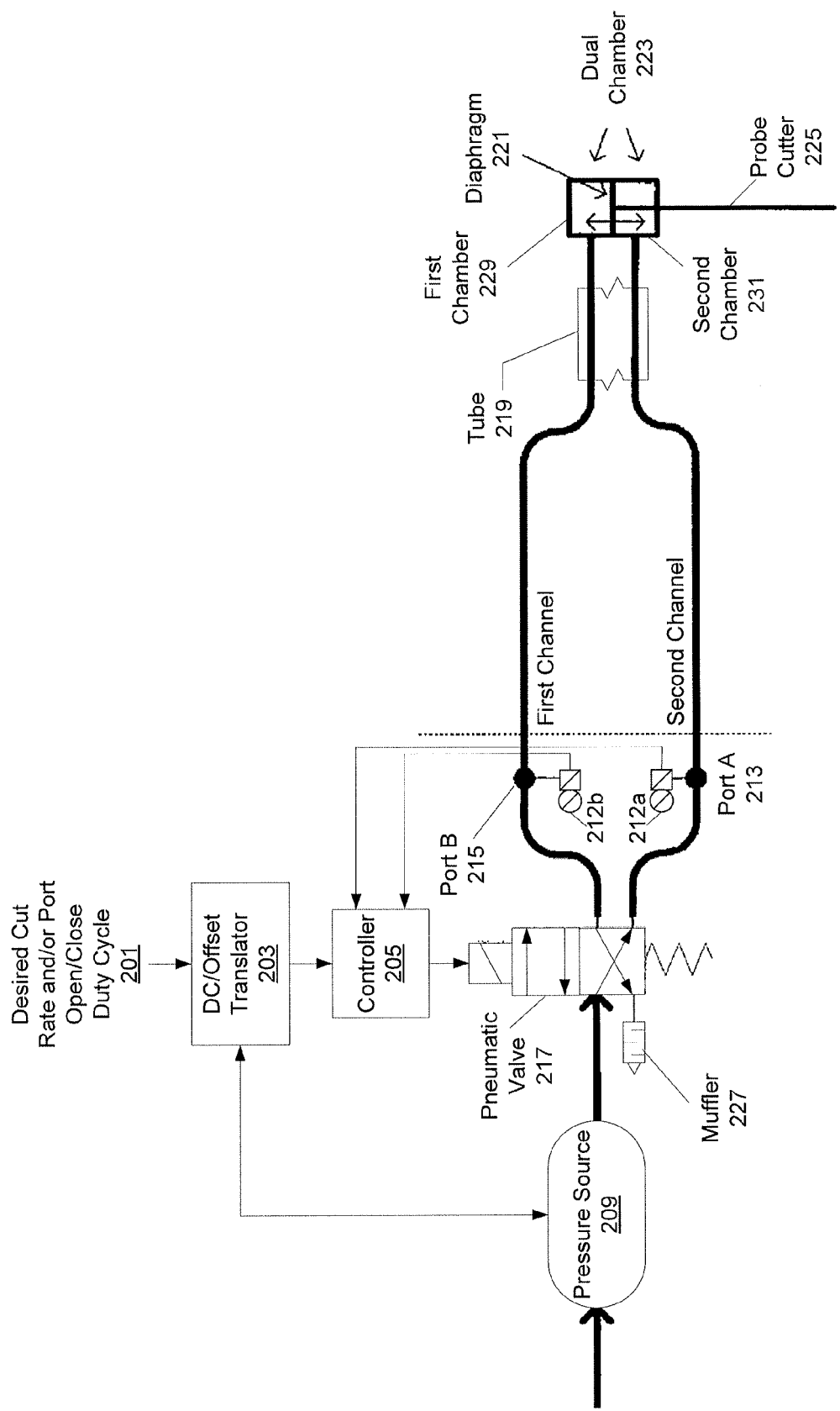
FIG. 2b is diagram of a pneumatic system with separate pressure sensors on each port, according to an embodiment.

Initially, a desired differential pressure (between port A and port B) may be determined based on user input (e.g., received through a user interface of the surgical console) or a system default stored in a memory on the surgical console 101 prior to valve operation. During valve operation, the controller 205 may modify the valve duty cycle of the valve 217 based on a detected/calculated actual differential pressure. For example, pressure sensor 211 may detect a pressure difference between port A 213 and port B 215 and send a signal indicative of the pressure difference to controller 205. In some embodiments, the pressure sensor 211 may calculate the average differential pressure 207 based on a detected differential pressure waveform or the pressure sensor 211 may relay the detected differential pressure waveform to the controller 205 and the controller 205 may determine the average differential pressure 207. In some embodiments, the average differential pressure 207 may be sent to the controller 205 as a signal that the controller 205 may interpret to derive the pressure (or, for example, use to derive other values related to pressure). While one pressure sensor 211 is shown in FIG. 2a, in some embodiments (e.g., as seen in FIG. 2b), each of port A 213 and port B 215 may have a separate pressure sensor (pressure sensors 212a,b) that may communicate with the controller 205. In some embodiments, the controller may receive pressure information from the pressure sensors 212a, b, calculate a differential waveform between the two ports and then determine an average differential pressure from the differential waveform. As another example, the controller may determine the offset of each pressure sensor output waveform to be used for controlling the valve duty cycle of the valve 217 (e.g., the controller may compare pressure information from the pressure sensors 212a,b to determine an average difference between the two port pressures). These differential pressures/average pressure differences may be used to determine how to dynamically adjust the VDC.

In some embodiments, the controller 205 may determine time intervals (corresponding to a modified valve duty cycle) to signal valve 217 to be in the first and second positions in order to achieve the desired average differential pressure between port A and port B. By applying an adjusted valve duty cycle to the cycle times for the pneumatic channels, the pneumatic channels may be actuated during the total cycle time to specific actual open times. As noted above, a 50% valve duty cycle may correspond to applying a signal (i.e., to energize the valve into the first position) for approximately the same amount of time as the signal is not applied (i.e., to de-energize the valve into the second position). An adjustment of 1% may result in a 51% valve duty cycle that corresponds to applying a signal to energize (i.e., to the first position) the valve for approximately 51% of the total cycle time (and 49% of the total time no signal is applied (to put the valve into the second position)). The longer 51% valve duty cycle may thus compensate, for example, for a valve that takes longer to move into the first position than it does to move into the second position and or a console that has higher flow restriction/resistance in the channel connecting to the first position of the valve. In some embodiments, the valve duty cycle may also be adjusted for various console characteristics (e.g., to compensate for the different transition times of various valves and flow restriction/resistance variations of various consoles).

In various embodiments, controller 205 may be configured to receive signals from pressure sensor 211 (or pressure sensors 212a,b) via an electronic interface (e.g., electrical conductors such as wires, buses, traces, or the like). Controller 205 may also be configured to send output signals via an electronic interface to pneumatic valve 217. These output signals may allow controller 205 to control the operation of pneumatic valve 217. Controller 205 may include an integrated circuit capable of performing logic functions. In this manner, controller 205 may be in the form of a standard integrated circuit package with power, input, and output pins. In various embodiments, controller 205 may include a valve controller or a targeted device controller. In some embodiments, controller 205 may perform specific control functions targeted to a specific device, such as a valve. In some embodiments, controller 205 may be a microprocessor. In such a case, controller 205 may be programmable so that it can function to control valves as well as other components of the console 101. In some embodiments, controller 205 is not a programmable microprocessor, but instead is a special purpose controller configured to control different valves that perform different functions.

Figure 4:
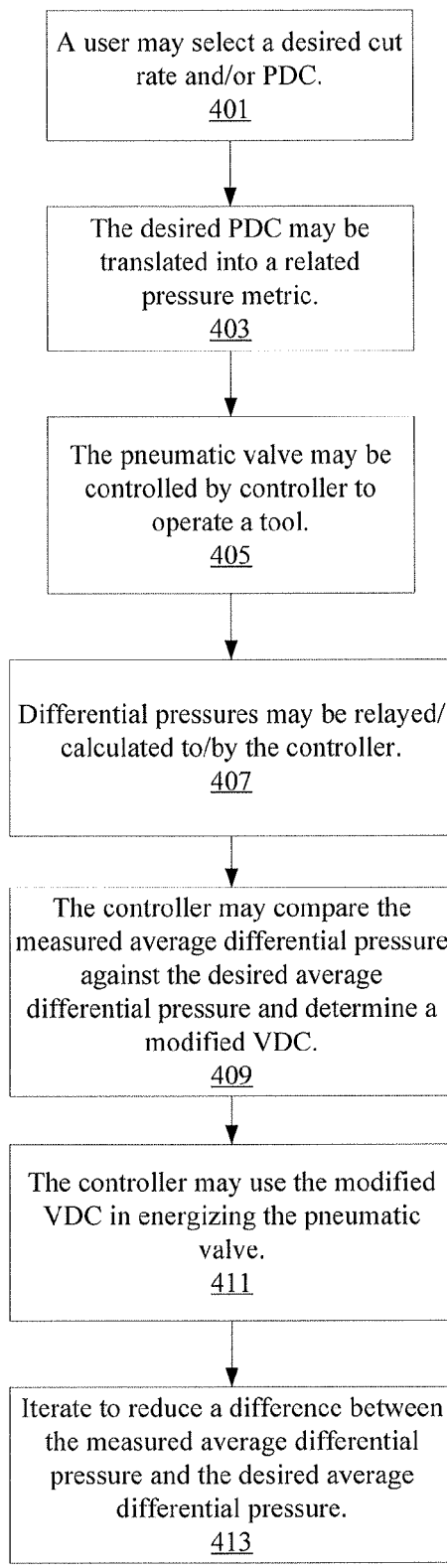
FIG. 4 illustrates a flowchart of a method for controlling a pneumatic valve, according to an embodiment.

FIG. 4 illustrates a flowchart of an embodiment of a method for dynamically controlling the pneumatic valve 217. The elements provided in the flowchart are illustrative only. Various provided elements may be omitted, additional elements may be added, and/or various elements may be performed in a different order than provided below.

At 401, a user may select a desired cut rate and/or PDC (e.g., based on surgical needs). For example, the user may enter a cut rate of 2500 cuts per minute at a PDC of 50%.

At 403, the desired PDC may be translated into a desired average differential pressure (or other pressure differences/metrics related to the differential pressure between ports A and B). In some embodiments, the desired PDC may be translated into a desired average differential pressure based on a pre-established look-up table (e.g., see FIG. 5), equation, etc. In some embodiments, the user may enter the desired average differential pressure into an interface on display 103. In some embodiments, the PDC and the desired average differential pressure may be provided as a default value (e.g., 50% PDC, 0 psi (pounds per square inch) desired average differential pressure). The average differential pressure may refer to an average differential pressure between port A and port B (taken as an average over time of the differential pressure waveform between port A and port B) or the difference between the port A average pressure and the port B average pressure. For example, PDC and corresponding average differential pressures may be determined experimentally, through trial and error, etc. for a valve. In some embodiments, other characteristics may be used to determine a desired average differential pressure (e.g., type of tool attached, etc).

At 405, the pneumatic valve 217 may be controlled by controller 205 to operate tool 103. In some embodiments, the controller 205 may initially control the valve 217 using a default valve duty cycle (e.g., 50%). In some embodiments, controller 205 may receive a desired average differential pressure from an offset translator 203 (e.g., an electronic circuit configured to convert a received electronic signal indicative of the desired PDC 201 into a corresponding desired average differential pressure based on an internal look-up table (e.g., see FIG. 5)). In some embodiments, controller 205 may receive other desired performance characteristics in addition to or in place of the desired average differential pressure (e.g., the controller may receive a desired difference between the average pressure waveforms from port A and port B or may receive a desired offset of port A pressure and port B pressure from a desired average pressure for the two ports).

At 407, average differential pressures 207 may be relayed from the pressure sensor 211 to the controller 205 (or calculated by the controller 205 using pressure information from pressure sensors 212a,b). For example, the average differential pressures 207 may be relayed by the pressure sensor 211 every 100 milliseconds (or pressure information (e.g., pressure offsets) may be relayed by pressure sensors 212a,b and the average differential pressure 207 may be calculated by the controller 205). Other time intervals are also contemplated (e.g., every 5 seconds). In some embodiments, the pressure sensor 211 may calculate the average differential pressure based on a detected differential pressure waveform or the pressure sensor 211 may relay the detected differential pressure waveform (which may include one or more differential pressures between port A and port B) to the controller 205 and the controller 205 may determine the average differential pressure 207. In some embodiments, pressure sensors 212a,b coupled to ports A and B may relay detected pressure information (e.g., pressure offset, pressure waveform, etc.) to the controller 205 and the controller 205 may determine the average differential pressure for the ports (or may compare the pressure waveforms without actually calculating the average differential pressure).

At 409, the controller 205 may compare the measured average differential pressure 207 (e.g., received from the pressure sensors or calculated using information from the pressure sensors) against the desired average differential pressure (e.g., calculated/determined from information received from the user or a default setting) and determine a modified VDC. The controller 205 may determine a modified VDC to reduce a difference between the desired average differential pressure and the measured average differential pressure. For example, if the pressure at port A is taken as positive pressure and the pressure at port B is taken as negative pressure, then for an ideal valve, the measured average differential pressure may be 0 psi. In this example, if the measured average differential pressure instead is positive (e.g., +2 psi), the measured average differential pressure may indicate that port A is actually staying open longer than port B during a given cycle (resulting in port A being charged to a higher pressure when open than port B charges to when open). If the desired average differential pressure was set at 0 psi, the VDC (which may indicate the percentage of the time the controller 205 signals port A to vent) may be increased by the controller 205 (e.g., from 50% to 51%). In some embodiments, the controller 205 may increase or decrease the VDC according to a default or user provided ratio. In some embodiments, the amount to adjust the VDC in response to the difference between the desired average differential pressure and the measured differential pressure may be experimentally determined for the valve 217. For example, it may be experimentally determined to increase VDC by 1% for every +1.2 psi difference between the measured average differential pressure and the desired average differential pressure (other ratios are also contemplated). This information may be stored in equation or table form accessible to the controller 205. As another example, the controller 205 may increase the VDC by a user provided increment (such as 0.5%) if the average differential pressure is positive and decrease the VDC by the user provided increment if the average differential pressure is negative. In some embodiments, the controller 205 may not adjust the VDC if the measured average differential pressure is within a default or user provided range (e.g., no adjustment if the average differential pressure is within 1 psi of the desired average differential pressure). In some embodiments, the user may enter various inputs for the controller's use (e.g., input into the touchscreen of display 109). For example, the user may enter a ratio of −1% VDC for every +1.2 psi difference between the measured average differential pressure and the desired average differential pressure. In some embodiments, the controller may not actually calculate differential pressures, but may instead compare pressure waveforms from port A and B (e.g., as determined by pressure sensors 212a,b) to each other or to desired waveforms to determine how to adjust the VDC. For example, if the pressure waveform for port A is, on average, 2 psi greater than a desired pressure waveform (e.g., as stored on the system), the VDC may be adjusted without having to actually calculate the differential pressure. Other VDC adjustment techniques are also contemplated.

At 411, the controller 205 may use the modified VDC in energizing the pneumatic valve 217 (e.g., to time the switch between the first/second positions).

At 413, the controller 205 may iterate between comparing the measured average differential pressure 207 against the desired average differential pressure (or related differential pressure variables/metrics) and determining a new modified VDC to minimize a difference between the measured average differential pressure 207 and the desired average differential pressure. For example, the controller 205 may implement a PID controller algorithm (Proportional-Integral-Derivative) to adjust the valve duty cycle upward or downward, receive a new detected average differential pressure (or receive new pressure information to use in calculating the average differential pressure), adjust the valve duty cycle correspondingly upward or downward based on the direction of the new average differential pressure as compared to the previous average differential pressure, receive/calculate a new average differential pressure in response to the modified valve duty cycle, etc. until the difference between the average differential pressure and the desired differential pressure is reduced (e.g., within a user provided range).

In some embodiments, the pneumatic management system may include one or more processors. The processor may include single processing devices or a plurality of processing devices. Such a processing device may be a microprocessor, controller (e.g., controller 205) (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. A memory coupled to and/or embedded in the processors may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory may store, and the processor may execute, operational instructions corresponding to at least some of the elements illustrated and described in association with the figures.

Figure 6:
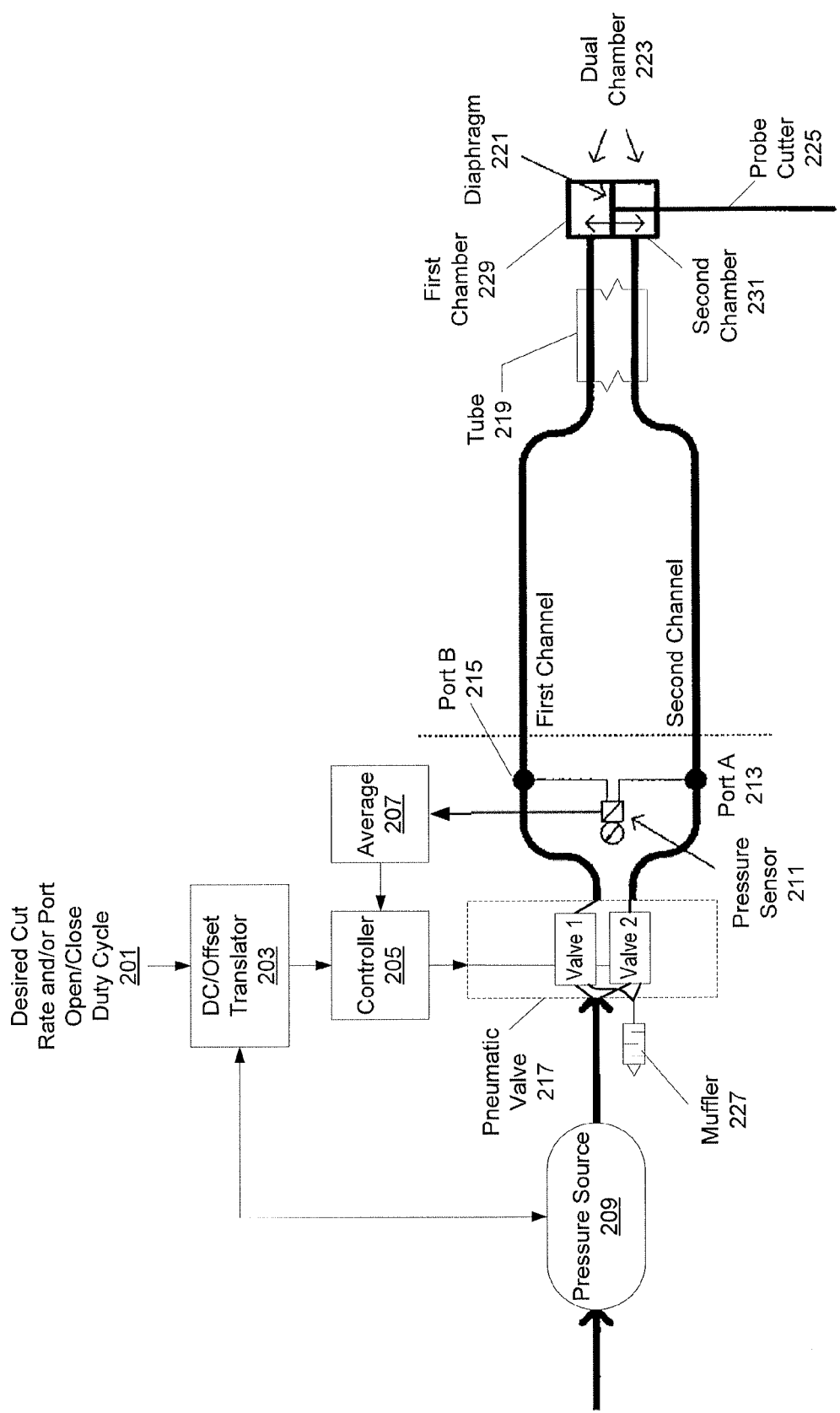
FIG. 6 illustrates an embodiment with a pneumatic valve including two or more valves.

As shown in FIG. 6, while several embodiments are described herein with respect to a four way pneumatic valve, it is to be understood these embodiments are also applicable to two or more valves being controlled in a coordinated fashion to provide pressurized gas to the tool 103. For example, the "first port" and the "second port" described with respect to a four-way pneumatic valve may instead be coupled to two or more separate valves (i.e., the "first port" coupled to a first valve and the "second port" coupled to a second valve). The first valve and second valve may be controlled together to provide pressurized gas alternately to the first port and the second port. In some embodiments, a pressure sensor may be coupled to both the first port and the second port to determine a differential pressure (or each port may be coupled to a separate pressure sensor and the separate pressures may be used in determining the average pressure). The valve duty cycle may then be used relative to the two or more valves to adjust the channel open and close times of their respective ports (by controlling the separate valves according to the open/close times indicated by the valve duty cycle).

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A surgical console, comprising:
   a pneumatic valve;
   at least a first port and a second port coupled to the valve, wherein the valve is configured to provide pressurized gas alternately to each of the first port and the second port;
   at least one pressure sensor coupled to at least one of the first port and the second port; and
   a controller coupled to the valve and the at least one pressure sensor, wherein the controller is operable to control valve channel open and close times according to a valve duty cycle;
   wherein the controller is configured to receive pressure data from the at least one pressure sensor;
   wherein the controller is configured to modify the valve duty cycle based on the received pressure data;
   wherein the controller is configured to receive pressure data from the at least one pressure sensor to use in determining a measured differential pressure between the first port and the second port and wherein the controller is configured to modify the valve duty cycle based on a difference between the measured differential pressure and a desired average differential pressure.

2. The surgical console of claim 1, wherein the pneumatic valve comprises two or more valves being controlled together to provide pressurized gas alternately to the first port and the second port and wherein controlling valve channel open and close times according to the valve duty cycle comprises controlling valve channel open and close times of the two or more valves according to the valve duty cycle.

3. The surgical console of claim 1, wherein a valve open time corresponds to a time to open a first port and wherein a valve close time corresponds to a time for closing the first port, wherein closing the first port coincides with opening a second port such that pressurized air is being directed by the valve either through the first port or the second port.

4. The surgical console of claim 1, wherein the at least one pressure sensor comprises a differential pressure sensor coupled to the first port and the second port to determine a differential pressure between the first port and the second port.

5. The surgical console of claim 1, wherein the controller receives pressure data from the at least one pressure sensor to use in determining a measured average differential pressure between the first port and the second port and uses the measured average differential pressure to modify the valve duty cycle at least twice during a continuous operating interval of the valve based on a difference between the measured average differential pressure and a desired average differential pressure.

6. The surgical console of claim 5, wherein a desired port duty cycle is received from a user through a user interface of the surgical console and wherein the desired port duty cycle is translated into a desired average differential pressure through an offset translator circuit.

7. The surgical console of claim 1, wherein the at least one pressure sensor comprises a first pressure sensor coupled to the first port and a second pressure sensor coupled to the second port and wherein the controller is configured to compare pressure information from the first pressure sensor and the second pressure sensor to modify the valve duty cycle.

8. The surgical console of claim 1, wherein the measured differential pressure comprises a measured average differential pressure.

9. The surgical console of claim 8, wherein the valve is configured to drive a pneumatic tool and wherein the surgical console further comprises a pneumatic tool coupled to the surgical console, wherein the pneumatic tool is a vitrectomy cutter.

10. The surgical console of claim 1, wherein a total valve time equals approximately the valve open time plus the valve close time for a valve cycle, and wherein the valve duty cycle is a percentage of the total valve time for the controller to signal the valve to direct gas through the first port.

11. The surgical console of claim 1, wherein the controller regulates pressure applied to the valve to balance between lower pressures for reducing air consumption and higher pressures for faster cut rates and increasing a dynamic range of available cut rates.

\* \* \* \* \*